US00PP33115P2

(12) United States Plant Patent
Clark

(10) Patent No.: US PP33,115 P2
(45) Date of Patent: Jun. 1, 2021

(54) BLACKBERRY PLANT NAMED 'CADDO'

(50) Latin Name: ***Rubus* subgenus *Rubus* Watson**
Varietal Denomination: Caddo

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 12 days.

(21) Appl. No.: 16/602,892

(22) Filed: Dec. 19, 2019

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 5/0887
See application file for complete search history.

(56) References Cited

U.S. PATENT DOCUMENTS

PP6,679 P 3/1989 Moore
PP8,510 P 12/1993 Moore
PP11,861 P2 5/2001 Clark et al.
PP11,865 P2 5/2001 Clark et al.
PP14,935 P2 6/2004 Clark
PP15,788 P2 6/2005 Clark
PP16,989 P3 8/2006 Clark et al.
PP17,162 P3 * 10/2006 Clark ..... A01H 6/7499 Plt./203
PP17,983 P2 9/2007 Cabrera Avalos
PP20,891 P3 3/2010 Clark
PP22,449 P3 1/2012 Clark
PP23,497 P3 3/2013 Clark et al.
PP24,249 P3 2/2014 Clark
PP25,864 P3 9/2015 Clark
PP26,120 P3 * 11/2015 Clark ..... A01H 6/7499 Plt./203
PP26,368 P3 2/2016 Banados Ortiz et al.
PP26,405 P3 2/2016 Clark et al.
PP26,413 P3 2/2016 Ortiz et al.
PP26,990 P3 8/2016 Clark
PP27,032 P2 8/2016 Clark
PP27,401 P3 11/2016 Clark et al.
PP28,598 P3 11/2017 Clark

OTHER PUBLICATIONS https://site.extension.uga.edu/viticulture/files/2019/02/Vol19-Issue1.pdf; Jan. 2019; 11 pages.*
First public announcement of cultivar on Jan. 2, 2019 at SE Fruit and Vegetable Conference in Savannah, GA.
Clark, J.R. & Worthington, M. "'Caddo' Thornless Blackberry" HortScience 2019 54(9):1632-1636.
News release on the Division of Agriculture, Cooperative Extension's Website was on Jan. 31, 2019: https://www.uaex.edu/media-resources/news/january2019/0125_Caddo_blackberry_released.aspx [nam03.safelinks.protection.outlook.com].
U.S. Appl. No. 16/602,884, filed Dec. 18, 2019.
PLUTO UPOVROM Plant Variety Database Citation for 'A-2491T' as per MX PBR 2781; Dec. 4, 2018; 1 page.

* cited by examiner

*Primary Examiner* — Kent L Bell
(74) *Attorney, Agent, or Firm* — Quarles & Brady LLP

(57) ABSTRACT

Description and specifications of a new and distinct cultivar of blackberry plant named 'Caddo' which originated from seed produced by a hand-pollinated cross of 'APF-45' (U.S. Plant Pat. No. 22,449) x Ark. '2108T' (non-patented, unreleased genotype). This new cultivar of blackberry plant can be distinguished by its large berries with very good fruit flavor, overall high fruit quality with excellent postharvest fruit-handling potential, early season ripening, consistent high yields, and excellent plant health.

3 Drawing Sheets

Latin name: *Rubus* subgenus *Rubus* Watson.
Varietal denomination: 'Caddo'.

BACKGROUND

The new floricane-fruiting cultivar of blackberry called 'Caddo' is described herein. The new cultivar originated from a hand-pollinated cross of 'APF-45' (U.S. Plant Pat. No. 22,449) x Ark. '2108T' (non-patented, unreleased genotype) made in 2004. The seeds resulting from this controlled hybridization were germinated in a greenhouse in the spring of 2005 and planted in a field near Clarksville, Ark. (West-Central Arkansas). The seedlings fruited in the summer of 2008 and one seedling, designated 'Caddo', was selected for its large berries with very good fruit flavor, overall high fruit quality with excellent postharvest fruit-handling potential, early season ripening, consistent high yields, and excellent plant health.

SUMMARY OF THE INVENTION

The new and distinct cultivar of blackberry originated from a hand-pollinated cross of 'APF-45' (U.S. Plant Pat. No. 22,449) x Ark. '2108T' (non-patented, unreleased genotype) made in 2004 and located near Clarksville, Ark. (West-Central Arkansas). The botanical designation of the new cultivar of blackberry is *Rubus* L. subgenus *Rubus* Watson. The seeds resulting from this controlled hybridization were germinated in a greenhouse in the winter to early spring of 2005 and planted in a field near Clarksville, Ark.

The seedlings fruited in the summer of 2008 on floricanes and one seedling, designated 'Caddo', was selected for its large berries with very good fruit flavor, overall high fruit quality with excellent postharvest fruit-handling potential, early season ripening, consistent high yields, and excellent plant health.

During 2008, the original plant selection was propagated asexually from root cuttings at the above-noted location, and a test row of 20 plants was established. Subsequently, larger test plantings have been established with asexually multiplied plants at two locations in Arkansas.

The new cultivar has been asexually multiplied annually since 2008 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants were three years old of which the pictures were taken.

DETAILED DESCRIPTION OF THE NEW CULTIVAR 'CADDO'

Figure 1:
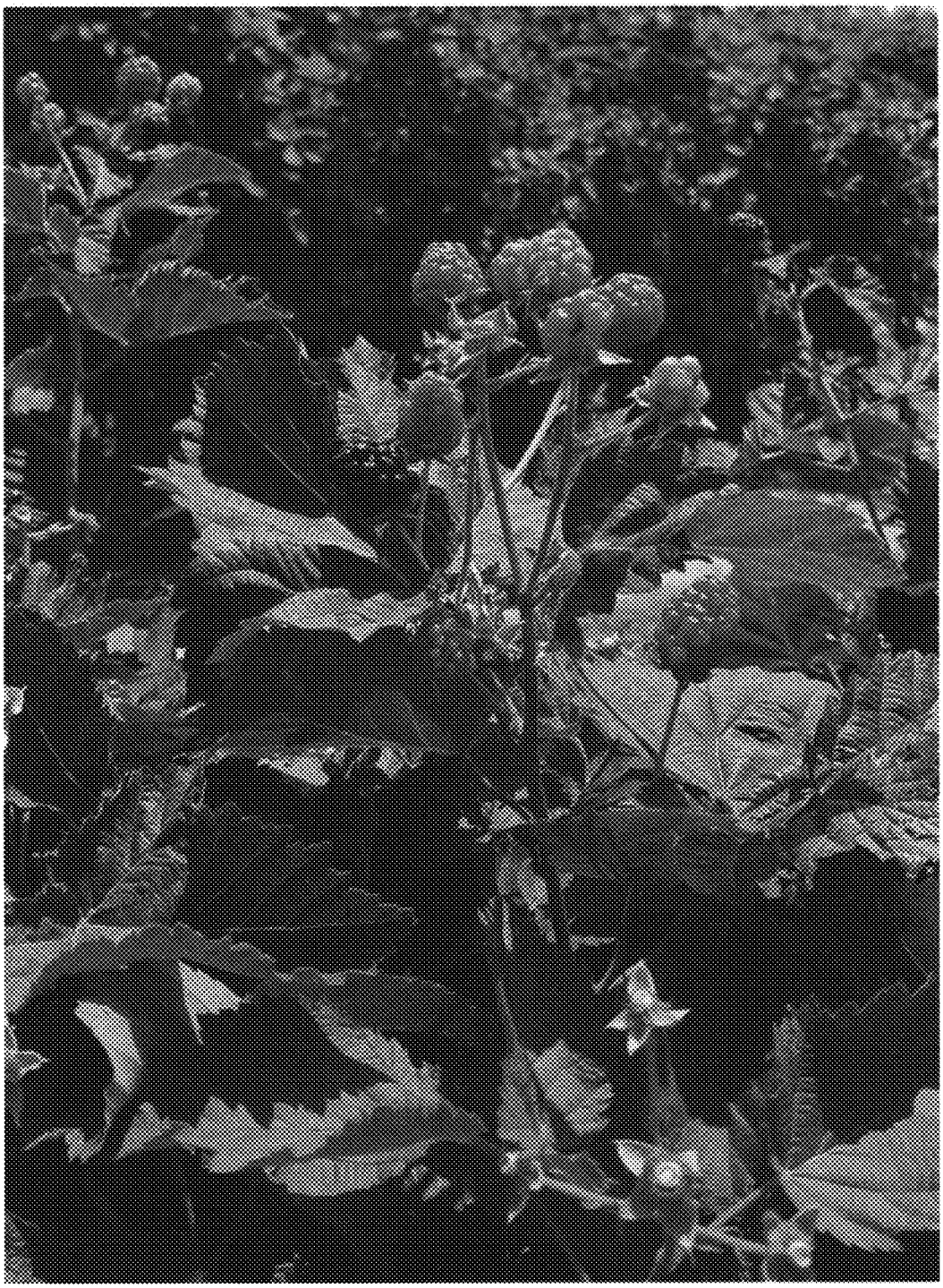
FIG. 1 is a photograph of blackberry canes of 'Caddo' with ripe fruit on the plant.
Figure 2:
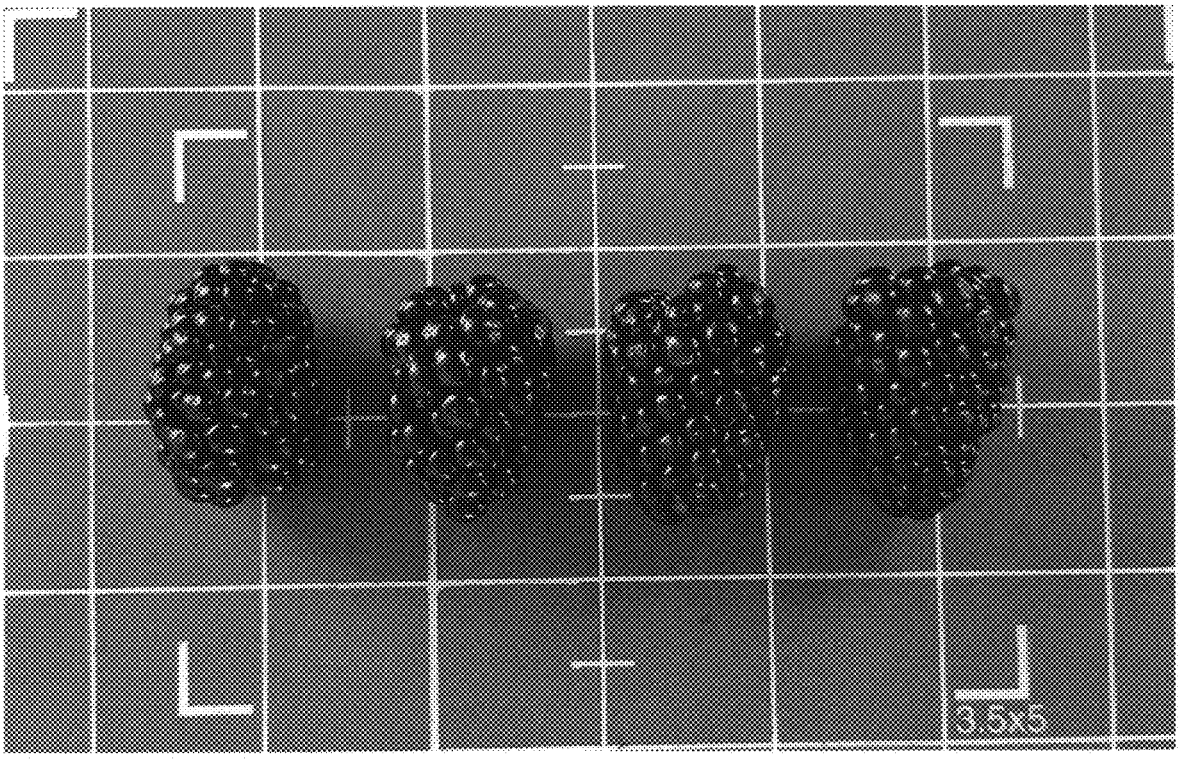
FIG. 2 is a photograph of ripe fruit of 'Caddo'.
Figure 3:
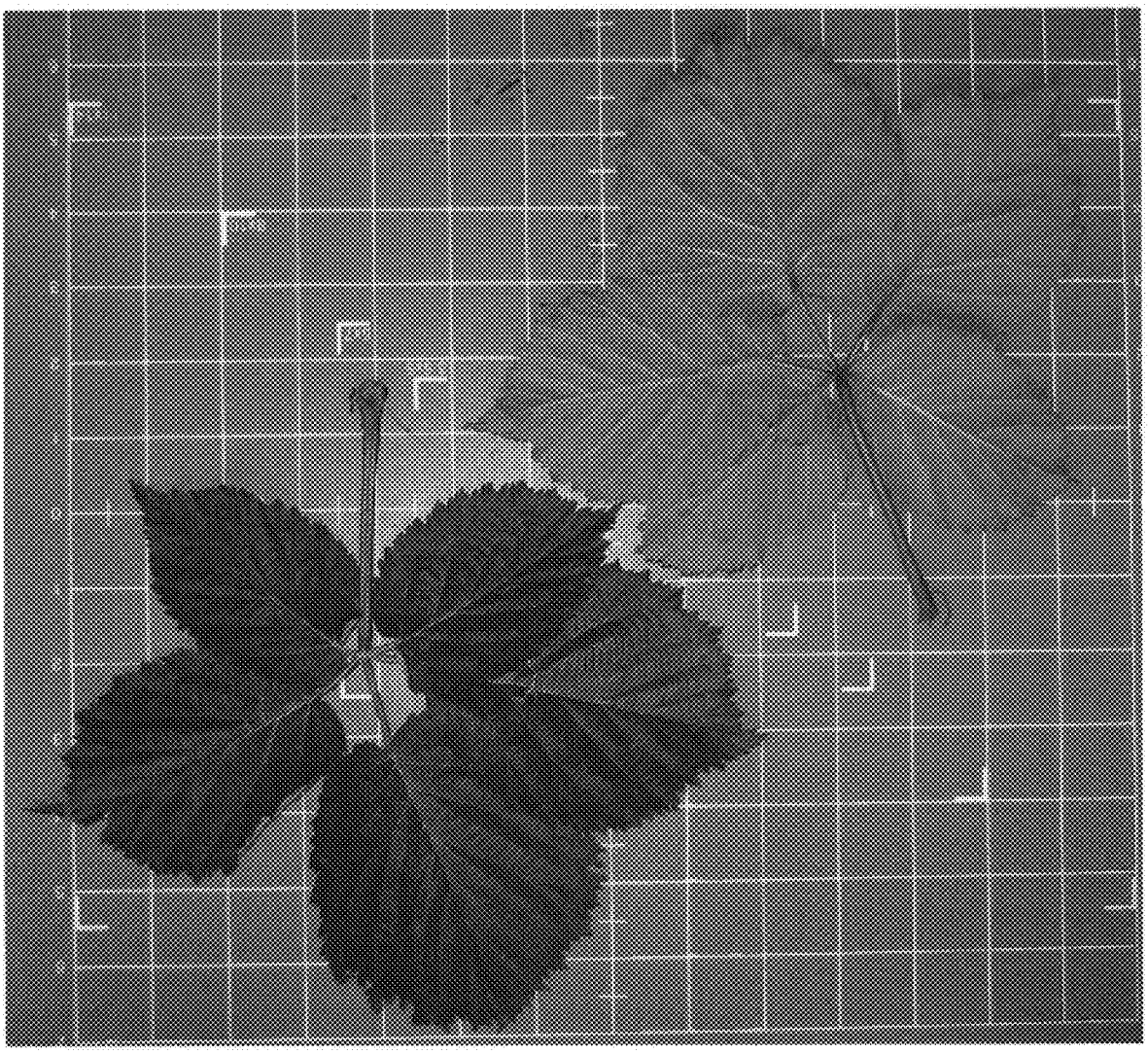
FIG. 3 is a photograph showing the abaxial and adaxial sides of a primocane leaf of 'Caddo'.

Plants and fruit of this new cultivar differ phenotypically from its parents. The new cultivar has thornless canes and is floricane fruiting compared to its female parent 'APF-45'. The new cultivar is earlier ripening, has larger fruit, and is more productive than its male parent Ark. '2108T'. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are thornless. Plants and fruit are resistant to anthracnose (*Elsinoe veneta* (Burkh.) Jenkins). Plants have shown no evidence of susceptibility to orange rust (*Gymnoconia nitens* (Schwein.) F. Kern and H. W. Thurston.). No screening has been done for resistance to double blossom/rosette (*Cercosporella rubi* (Wint.) Plakidas)

The bloom period of the new cultivar begins on average 27 April for 10% bloom and 2 May for 50% bloom and was very near that of 'APF-45', 'Osage' (U.S. Plant Pat. No. 26,120) and 'Ouachita' (U.S. Plant Pat. No. 17,162).

Fruit of the new cultivar has an average first harvest date of 8 June and was very near that of 'APF-45', two days earlier than 'Osage' and five days earlier than 'Ouachita'. The average floricane fruiting period is 40 days.

Fruit yields of the new cultivar on floricanes are on average 5.0 kg (11.0 lb/plant), comparable to that for 'Osage' and 'Ouachita', in West-Central Arkansas.

The fruit is oblong and glossy with a uniform black finish. The floricane fruit is large (ave. 8.0 g) usually 2.0 g or more, larger than its similar-season comparison cultivar 'Osage', and 1.0 to 1.5 g larger than 'Ouachita'. Fruit size of the new cultivar is maintained well throughout the entire harvest season. The new cultivar exhibits excellent fruit fertility with full drupelet set. Fruit firmness is a noteworthy characteristic as firmness was consistent whether in rainy or dry periods of fruit maturity. Storage potential of fresh fruit of the new cultivar is comparable to that of 'Osage' and 'Ouachita'.

The dry seed weight for the new cultivar averaged 4.3 mg/seed, slightly smaller than 'APF-45' (4.5 mg), 'Ouachita' (4.5 mg) and slightly larger than 'Osage' (3.8 mg).

The fresh fruit rates very well in flavor and is a noteworthy attribute of the cultivar and is comparable to or exceeding that of 'PAF-45', 'Osage', and 'Ouachita'. Consistent excellent flavor was noted at repeated observations of fruit of this cultivar over the years of evaluation, including after rain events that can reduce flavor and overall fruit quality. The flavor is sweet and mildly acidic, with desirable aromatics. The soluble solids concentration averages 9.8% on shiny black fruit, comparable to 'APF 45', 'Osage', and 'Ouachita'. Fruit and flower clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in Royal Horticultural Society Color Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation at or near Clarksville, Ark. The plants were fertilized near budbreak (late March on average) with complete or nitrogen fertilizer, and had an additional nitrogen fertilizer application in early July. Primocanes were tipped at approximately 1.14 m (45 inches) and grown in a hedgerow training system. Weeds were controlled with pre- and post-emergence herbicides supplemented with mechanical weed control activities. A single application of liquid lime sulfur was applied to the plants at budbreak, but no other fungicides were used. The descriptions reported herein are from specimens grown near Clarksville, Ark.

Plant:

*Size.*—Medium. Plants are grown in a hedgerow and primocanes tipped at approx., 1.14 m; plants in this system range in size from approx. 107-140 cm tall and 91-102 cm wide.

*Growth habit.*—Upright, moderate vigor, canes erect; suckers from the crown.

*Growth rate.*—Floricane first budbreak 20 February; first emergence of primocanes is 15 March and primocanes reach tipping height (107 cm) on 1 May.

*Productivity.*—Floricane — 5.0 kg/plant (11.0 lb).

*Cold hardiness.*—Hardy to 1.4° F. (−17° C.) or lower. The low temperature of 1.4° F. was the lowest the cultivar has been exposed to and fruited successfully after this exposure.

*Canes.*—Thornless, erect. Floricane (dormant or winter cane): Cane diameter: base 1.57 cm; midpoint 1.30 cm; terminal 1.03 cm. Internode length: base 3.03 cm; midpoint 5.08 cm; terminal 3.42 cm. Floricane color: base Grayed Purple (183A); midpoint Grayed Purple (183A); terminus Grayed Purple (183A). Primocane (current-season cane; late summer): Cane diameter: base 1.45 cm; midpoint 1.14 cm; terminal 0.49 cm. Internode length: base 5.88 cm; midpoint 6.14 cm; terminal 2.27 cm. Primocane color: base Red Purple Group (59A)· midpoint Yellow Green Group (146B) over Red Group (sun exposed); terminus Yellow Green Group (146B) over Red Group 59-A (sun exposed). Anthocyanin coloration present on floricanes and primocanes with color most prevalent on sun-exposed canes. Thorn density (per 30 cm of cane length): plant is thornless. Lateral branching after tipping (measured at the end of growing season): Average number of lateral branches: 7.5; distribution full length of cane. Disease resistance: Moderate resistance to anthracnose, and no evidence of orange rust disease. Lower susceptibility to leaf rust. No screening has been done for resistance to double blossom/rosette.

Foliage:

*Primocane.*—Leaves: large; mature compound leaf width 24.9 cm; length 20.9 cm. Leaf shape: Compound leaf shape palmate. Glossiness: Abaxial: dull, pubescence lightly present; adaxial: moderate gloss, pubescence lightly present. Leaflet: Width 9.83 cm; length 11.5 cm; shape cordate with acute apex and cordate base; margin serrated, serration teeth length 0.28 cm and width 0.33 cm; number of leaflets per compound leaf 5; venation pinnate; young leaf abaxial vein color Yellow Green Group 147-C; young leaf adaxial vein color Yellow Green Group 147-B; mature leaf abaxial leaf vein color 147C; material leaf adaxial vein color Yellow Green Group 147C; no lobing on leaflets. Color: Base abaxial Green Group (137C); adaxial Green Group (139A); midpoint abaxial Green Group (137C); adaxial Green Group (139A); terminal abaxial Green Group (137C); adaxial Green Group (139A). Petioles: Length: 8.77 cm; color: adaxial Green Group (137C) and abaxial Red Purple Group (59B); diameter 0.4 cm; texture is light pubescence. Petiolules: Length: 3.47 cm; diameter 0.22 cm; color: adaxial Green Group (137B) over abaxial Green Group (137D); texture is light pubescence. Stipules: 2 per leaf; Length: 1.98 cm; width: 0.13 cm; texture pubescence is moderate on abaxial surface and heavy on adaxial surface. Shape: overall shape linear; apex acute; base cruncate; margin: entire (smooth). Color: Green Group (139A) over Green Group (139B).

*Floricane.*—Leaves: Medium; mature compound leaf width 11.90 cm; length 10.28 cm. Leaf shape: Compound leaf shape palmate. Glossiness: Abaxial: dull, pubescence moderately present; adaxial: moderate gloss, pubescence lightly present. Leaflet: Width 4.93 cm; length 6.63 cm; shape cordate with acute apex and cordate base; margin serrated, with serration teeth length 0.29 cm and width at base 0.41 cm; number of leaflets per compound leaf 3; venation pinnate; young leaf abaxial vein color Yellow Green Group 147-C; young leaf adaxial vein color Yellow Green Group 147-B; mature leaf abaxial leaf vein color 147D; mature leaf adaxial vein color Yellow Green Group 146C; no lobing on leaflets. Color: base abaxial Green Group (147B); adaxial Green Group (137A); midpoint abaxial Green Group (147B); adaxial Green Group (137A); terminal abaxial Yellow Green Group (147B); adaxial Green Group (137B). Petioles: Length 4.92 cm; color: Yellow Green Group (147B) over Red Purple Group (53A); diameter 0.21 cm; texture pubescence is light on adaxial side and heavy on abaxial side. Petiolules: Length 1.04 cm; diameter 0.12 cm; Color: Yellow Green Group (147B) over Red Purple Group (60-A); diameter 0.4 cm; texture is light pubescence. Stipules: 2 per leaf; length 1.10 cm; width: 0.23 cm; texture pubescence is moderate on abaxial side and light on adaxial side. Shape: overall shape linear; apex acute; base cruncate; margin: entire (smooth); Color: Yellow Green Group (147B) over Yellow Green Group (146B).

Flowers:

*Floricane.*—Date of bloom: First bloom 27 April; 50% bloom 2 May. Petal color: White Group (155D) with Grayed Purple group (186C) on tip; identical color on both sides of petals. Reproductive organs: Stamens — erect, numerous. Pistils — numerous. Pollen — normal, fertile, and abundant. Flower diameter: 3.96 cm. Flower shape: regular, radially symmetrical and actinomorphic. Flower depth: 1.70 cm. Petal size: Length 2.21 cm; width 1.74 cm. Petal Shape: Overall: obovate; apex: rounded; margin: entire (smooth); base: cuneate. Petal Texture: Abaxial: no pubescence; adaxial; no pubescence. Average number flowers per cluster: 7. Average number of petals per flower: 15. Number of sepals per flower: 5. Sepal: Length 1.0 cm; width: 0.57 cm. Sepal shape: Overall: lanceolate; apex: aristate; margin: entire (smooth); base: truncate. Sepal texture: Abaxial: moderate pubescence; adaxial: heavy pubescence. Sepal color: Abaxial: Yellow Green group (144A) with tip Red Purple Group 64-A; adaxial: Green Green Group group (148B). Pedicel: Length: 1.50 cm; width: 0.01 cm; Color: Yellow-green group (146C); texture: heavy pubescence. Peduncle length: 4.03 cm. Peduncle width: 0.09 cm. Peduncle color: Yellow-Green Group (146B). Cyme type: Simple cyme. Cyme length: 8.02 cm.

*Fruit: Maturity — Average first ripe date* 8 June; average fruiting period 40 days. Size: Large, average 8.0 g. Diameter of fruit at primary position on inflorescence: equator 2.03 cm; base pole 1.79 cm; terminal pole 1.07 cm. Diameter of fruit at secondary positions on inflorescence: equator 1.87 cm; base pole 1.63 cm; terminal pole 1.43 cm. Length (primary fruit): 2.97 cm. Shape: oblong. Color: Black Group (202A). Drupelet size: 0.57 cm. Drupelet number per fruit: 71.6. Seed: average length 0.41 cm; width 0.24 cm; dry weight 4.3 mg; color wet Grayed Orange Group (164C); color dry Grayed Orange Group (164D). Soluble solids: 9.8%. pH: 2.98. Acidity: 1.01 g/L (expressed as citric acid).

Processed quality: Not evaluated for processing. Uses: Commercial cultivar with good potential for shipping, as well as an option for local-market production as well as home gardens.

The cultivar: The most distinctive features of the cultivar are large berries with very good fruit flavor, overall high fruit quality with excellent postharvest fruit-handling potential, early season ripening, consistent high yields, and excellent plant health.

I claim:

1. A new and distinct cultivar of blackberry plant named 'Caddo', substantially as illustrated and described herein.

* * * * *